US00PP27631P3

(12) United States Plant Patent
Helvick et al.

(10) Patent No.: US PP27,631 P3
(45) Date of Patent: Jan. 31, 2017

(54) ***DISTYLIUM* PLANT NAMED 'PIIDIST-V'**

(50) Latin Name: ***Distylium* sp. hybrid**
Varietal Denomination: PIIDIST-V

(71) Applicant: Plant Introductions, Inc., Watkinsville, GA (US)

(72) Inventors: Rhonda Helvick, Madison, GA (US); Oren McBee, Bishop, GA (US); Mark Griffith, Watkinsville, GA (US); Jeff Beasley, Lavonia, GA (US); Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 179 days.

(21) Appl. No.: 14/121,508

(22) Filed: Sep. 12, 2014

(65) Prior Publication Data

US 2016/0081245 P1 Mar. 17, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Lathrop & Gage LLP

(57) ABSTRACT

A new and distinct cultivar of *Distylium* plant named 'PIIDIST-V', characterized by its compact, layered, and mounding growth habit, reddish new growth, blue-green mature foliage, and cold tolerance.

2 Drawing Sheets

Genus and species of plant claimed: *Distylium* sp. hybrid. Variety denomination: 'PIIDIST-V'.

BACKGROUND OF THE INVENTION

The present invention relates to a new and distinct cultivar of *Distylium* plant, botanically known as *Distylium* hybrid, a member of the Hamamelidaceae, and hereinafter referred to by the cultivar name 'PIIDIST-V'.

'PIIDIST-V' originated as an open-pollinated seedling from seed collected from *Distylium* hybrid 'PIIDIST-II' (U.S. Plant Pat. No. 24,409) growing in Watkinsville, Ga. 'PIIDIST-V' is a *Distylium* sp. hybrid (*Distylium myricoides*×*D. racemosum* which was confirmed by DNA testing) and was selected in the summer of 2012 by the inventor in a cultivated environment in Watkinsville, Ga.

Asexual reproduction of 'PIIDIST-V' by stem cuttings in Watkinsville, Ga. since 2012 has shown that all the unique features of 'PIIDIST-V', as herein described, are stable and reproduced true-to-type through successive generations of such asexual propagation.

SUMMARY OF THE INVENTION

Plants of the new cultivar 'PIIDIST-V' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIDIST-V'. These characteristics in combination distinguish 'PIIDIST-V' as a new and distinct cultivar: 1. Compact, layered, and mounding growth habit; 3. Reddish new growth; 3. Small strapped-shaped, blue-green foliage on mature growth; and 4. Increased cold hardiness compared to the parent.

Plants of 'PIIDIST-V' differ from plants of the parent, *Distylium* hybrid 'PIIDIST-II' (U.S. Plant Pat. No. 24,409), primarily in growth habit, foliage color, foliage size, as plants of 'PIIDIST-V' have smaller, more compact, mounding growth habit and smaller, linear-ovate, blue-green foliage, and increased cold tolerance to −15° C. 'PIIDIST-II' (U.S. Plant Pat. No. 24,409) has larger blue-green leaves, an open, larger growth habit, stems that are more upright, and is less cold tolerant to −12° C.

Plants of the new *Distylium* 'PIIDIST-V' can be compared to plants of the cultivar 'Vintage Jade' (U.S. Plant Pat. No. 23,128), 'Vintage Jade' has a compact, layered, mounding, and spreading growth habit, light green new growth, lustrous dark green mature foliage, and larger leaves, whereas 'PIIDIST-V' has a compact, layered growth habit, reddish new growth, blue-green mature foliage, and mature size one-half that of that of 'Vintage Jade'.

BRIEF DESCRIPTION OF THE DRAWINGS

The accompanying color photographs illustrate the foliage characteristics and the overall appearance of 'PIIDIST-V', showing the colors as true as it is reasonably possible to obtain in color reproductions of this type. Colors in the photographs may differ slightly from the color values cited in the detailed botanical description which accurately describe the colors of 'PIIDIST-V'.

DETAILED DESCRIPTION

Figure 1:
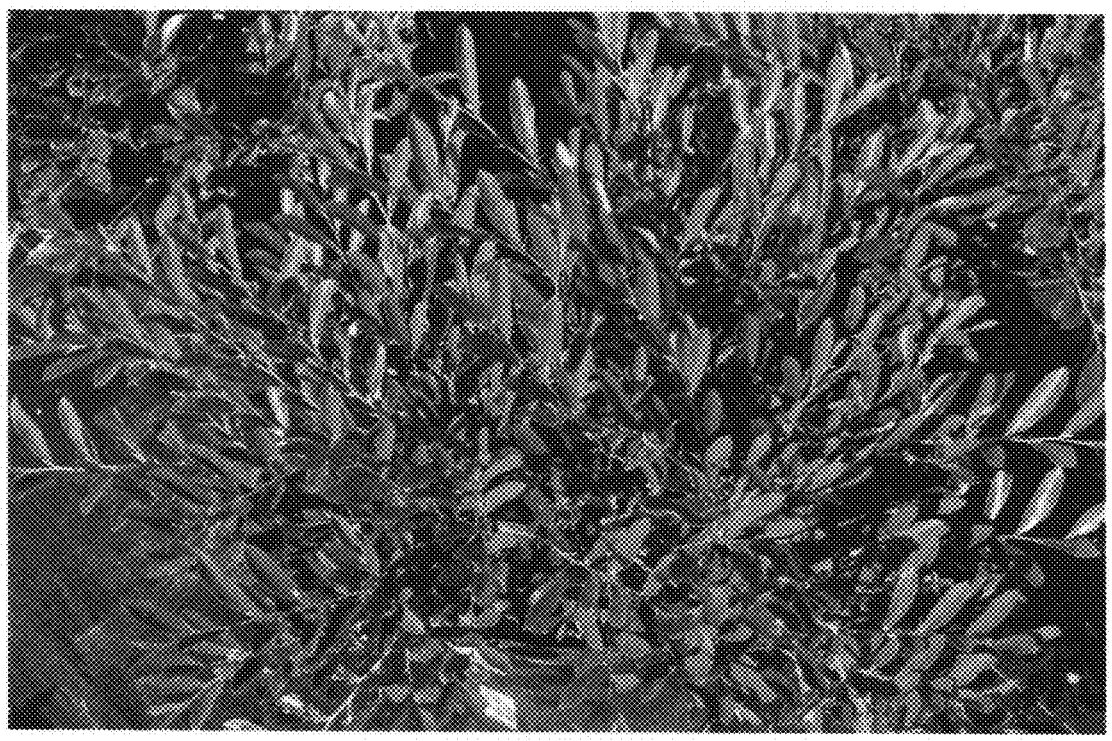
FIG. 1 illustrates the overall appearance and growth habit of a three-year-old 'PIIDIST-V' plant.
Figure 2:
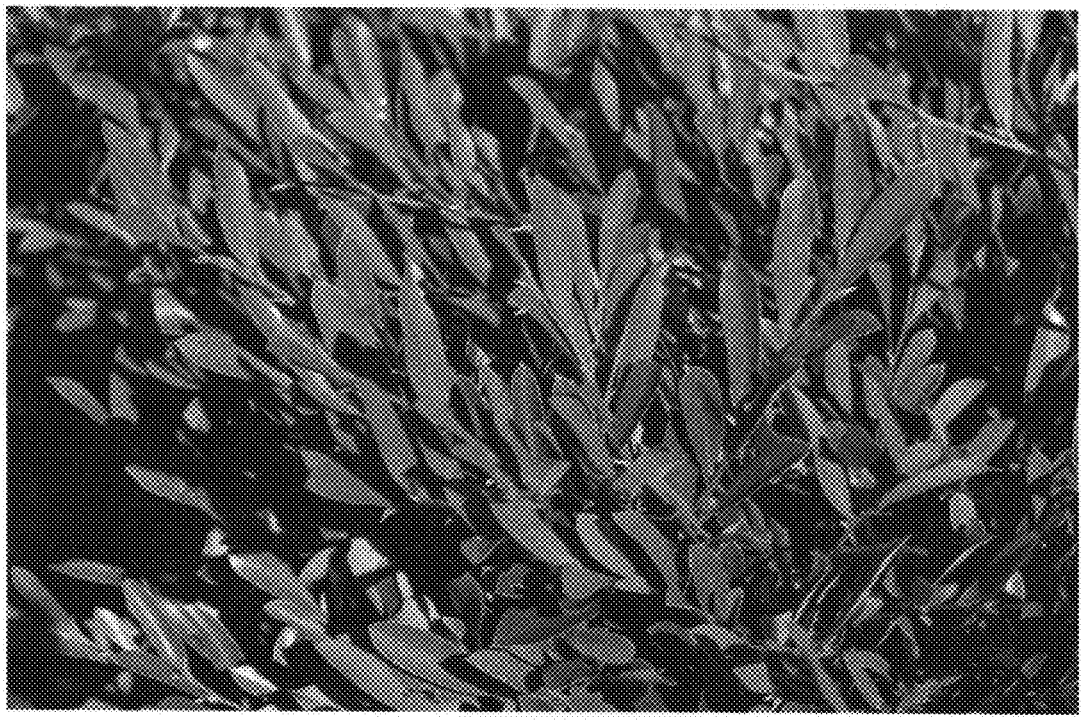
FIG. 2 illustrates a close-up of the new growth and mature foliage of a three-year-old 'PIIDIST-V' plant.

In the following description, color references are made to The Royal Horticultural Society Colour Chart, 2007 Edition, except where general terms of ordinary dictionary significance are used. The plant used for the description was approximately three-years-old and was grown in the ground under outdoor conditions in Watkinsville, Ga.

Botanical classification: *Distylium* hybrid, cultivar 'PIIDIST-V'.

Parentage:

*Female, or seed, parent.*—*Distylium* hybrid 'PIIDIST-II' (U.S. Plant Pat. No. 24,409).

*Male, or pollen Parent.*—Unknown (open-pollinated).

Propagation: Stem cuttings.

*Time to initiate roots in summer.*—About 3 to 4 weeks at 32° C.

*Time to produce a rooted young plant, in summer.*—About 4 months at 32° C.

Plant description: Broadleaf evergreen shrub; multi-stemmed; compact, mounding and spreading growth habit. Freely branching; removal of the terminal bud enhances lateral branch development.

*Root description.*—Medium, well-branched, diffuse and extensive.

*Plant size.*—The original plant, now about three-years-old in the ground, is about 47 cm high from the soil level to the top of the foliage and about 90 cm wide.

*First year stems.*—Having a diameter of about 2 mm. Length: 21 cm and stems flexible. Shape: round. Fine pubescence. Few small lenticels about 1 mm in diameter and N199B in color.

*First year stem color.*—146A.

*Second year and older stems.*—Have a diameter of about 3 mm or more. Length: 65 cm and stems easily broken once mature. Smooth, no pubescence. Shape: round.

*Second year and older stem color.*—N200A.

*Stem strength.*—Flexible when young, less flexible once mature.

*Internode length.*—About 1.4 cm.

*Trunk diameter.*—About 4 cm at the soil line.

*Color.*—199B.

*Bark.*—Does not exfoliate, covered with many lenticels, N199B in color, about 1 mm in diameter.

Vegetative bud description:

*Arrangement.*—Alternate.

*Shape.*—Ovoid with fused, pubescent bud scales.

*Size.*—About 2 mm in length and about 1 mm in width.

*Color.*—200A.

Foliage description:

*Arrangement.*—Alternate, simple.

*Length.*—About 5 cm.

*Width.*—About 12 mm.

*Shape.*—Ovate-lanceolate.

*Apex.*—Acute.

*Base.*—Cuneate.

*Margin.*—Entire, occasionally undulating.

*Texture* (*upper and lower surfaces*).—Smooth, thick, leathery.

*Venation pattern.*—Pinnate.

*Venation color* (*upper and lower surfaces*).—Midrib color is 147B and secondary vein color is 147A.

*Color of emerging foliage* (*upper surface*).—183A.

*Color of emerging foliage* (*lower surface*).—147C.

*Color of mature foliage* (*upper surface*).—139A.

*Color of mature foliage* (*lower surface*).—139C.

*Petiole length.*—About 4 mm.

*Petiole diameter.*—About 1 mm. Fine pubescence 199A in color.

*Petiole color* (*upper and lower surfaces*).—139C.

Flower description: The original plant is three-years-old and has not flowered to date.

Fruit: The original plant is three-years-old and has not produced fruit to date.

Plant hardiness:

*Plant hardiness.*—USDA Hardiness Zone Map (2012): Zones 7-9.

Disease/pest resistance:

*Disease and pest resistance.*—Not observed to be susceptible nor resistant to normal disease and pest of *Distylium.*

I claim:

1. A new and distinct *Distylium* plant named 'PIIDIST-V', as illustrated and described herein.

* * * * *